(12) United States Patent
Lucchina et al.

(10) Patent No.: US 10,145,748 B2
(45) Date of Patent: Dec. 4, 2018

(54) PRESSURE INDICATOR

(75) Inventors: Pascal Lucchina, Bordeaux (FR);
Stéphane Checcaroni, Nice (FR);
Gilles Dhonneur, Le Plessis Trevise (FR)

(73) Assignee: AMBU A/S, Ballerup (DK)

( * ) Notice: Subject to any disclaimer, the term of this patent is extended or adjusted under 35 U.S.C. 154(b) by 560 days.

(21) Appl. No.: 14/125,532

(22) PCT Filed: Jun. 11, 2012

(86) PCT No.: PCT/EP2012/061032
§ 371 (c)(1),
(2), (4) Date: Apr. 7, 2014

(87) PCT Pub. No.: WO2012/171881
PCT Pub. Date: Dec. 20, 2012

(65) Prior Publication Data
US 2014/0230824 A1    Aug. 21, 2014

(30) Foreign Application Priority Data
Jun. 11, 2011    (FR) ...................................... 11 01808

(51) Int. Cl.
*A61M 16/00* (2006.01)
*A61M 16/04* (2006.01)
(Continued)

(52) U.S. Cl.
CPC .......... *G01L 7/084* (2013.01); *A61B 17/3401* (2013.01); *A61M 5/16854* (2013.01);
(Continued)

(58) Field of Classification Search
CPC .. A61M 16/00; A61M 16/0003; A61M 16/04; A61M 16/0402; A61M 16/0409;
(Continued)

(56) References Cited

U.S. PATENT DOCUMENTS 3,241,514 A    3/1966  Grimland
3,675,722 A    7/1972  Balmes, Sr.
(Continued)

FOREIGN PATENT DOCUMENTS

CN    2203128    7/1995
CN    1942612    4/2007
(Continued)

OTHER PUBLICATIONS

European Patent Office International Search Report and Written Opinion dated Sep. 14, 2012, International Application No. PCT/EP2012/061032 (11 pages).

*Primary Examiner* — Gregory Anderson
*Assistant Examiner* — Ned T Heffner
(74) *Attorney, Agent, or Firm* — Faegre Baker Daniels LLP

(57) ABSTRACT

Pressure indicator comprising a base, a deformable membrane fixed to the base in a fluid-tight manner according to a closed contour, and a body fixed to the base, delimiting a hollow volume covering the deformable membrane on the side opposite the base, while encompassing at least the closed contour, at least one inlet for a fluid the pressure of which is to be measured in a pressure range, wherein the deformable membrane is such that the expansion thereof for said pressure range is sufficient to be visible to the naked eye and to allow a direct display indicative of the pressure, in that the base is drilled with at least one first hole a first end of which emerges between the deformable membrane and the base in the closed contour, in that the body is drilled with at least one second hole a first end of which emerges into said hollow volume, in that the other end of the first hole is linked to the inlet respectively to the open air, in that the other end of the second hole is linked to the open air, respectively to the inlet, so that a pressure, respectively a pressure reduction, of fluid at the inlet causes an expansion
(Continued)

of the deformable membrane in the hollow volume delimited by the body. Application of such an indicator to the monitoring of the inflation of a medical apparatus pad.

20 Claims, 9 Drawing Sheets

(51) Int. Cl.
*G01L 7/08* (2006.01)
*G01L 19/12* (2006.01)
*A61B 17/34* (2006.01)
*A61M 5/168* (2006.01)
*A61B 5/03* (2006.01)

(52) U.S. Cl.
CPC ...... *A61M 16/0003* (2014.02); *A61M 16/044* (2013.01); *A61M 16/0409* (2014.02); *A61M 16/0434* (2013.01); *A61M 16/0447* (2014.02); *G01L 7/086* (2013.01); *G01L 19/12* (2013.01); *A61B 5/036* (2013.01); *A61B 5/038* (2013.01); *A61M 2016/0027* (2013.01)

(58) Field of Classification Search
CPC .......... A61M 16/0411; A61M 16/0415; A61M 16/042; A61M 16/0434–16/0459; A61M 16/0463; A61M 16/0465; A61M 16/0472; A61M 16/0475–16/0486; A61M 16/08; A61M 2016/0027; A61M 25/00; A61M 25/1018–25/10188; A61M 2025/002; A61M 2025/0003; A61M 2025/1047; A61M 3/00; A61M 29/00; A61B 5/03; G01L 9/0033–9/008

See application file for complete search history.

(56) References Cited

U.S. PATENT DOCUMENTS

| 3,703,879 | A | | 11/1972 | Huthsing, Jr. | |
|---|---|---|---|---|---|
| 4,166,430 | A | * | 9/1979 | Johnson, Jr. | G01D 5/28 116/202 |
| 4,502,491 | A | * | 3/1985 | Ender | A61B 5/03 116/270 |
| 4,819,686 | A | * | 4/1989 | Achterholt | B60C 23/0496 116/34 R |
| 4,873,990 | A | * | 10/1989 | Holmes | A61B 5/036 600/488 |
| 5,255,670 | A | * | 10/1993 | Lomholt | A61M 16/044 128/200.24 |
| 5,365,967 | A | * | 11/1994 | Moore | B60C 23/0496 116/34 R |
| 7,530,273 | B1 | * | 5/2009 | Conklin | G01D 5/268 73/705 |
| 2006/0076021 | A1 | | 4/2006 | Chang | |
| 2009/0091066 | A1 | * | 4/2009 | Sleva | A61M 16/0445 264/521 |
| 2009/0099545 | A1 | * | 4/2009 | Nilsson | A61M 5/14244 604/506 |

FOREIGN PATENT DOCUMENTS

| CN | 201179260 | 1/2009 |
|---|---|---|
| DE | 3832252 | 1/1990 |
| DE | 4116709 | 11/1992 |
| EP | 0228068 | 7/1987 |
| FR | 1566635 | 5/1969 |
| FR | 2475726 | 8/1981 |
| GB | 1261048 | 1/1972 |
| GB | 1464271 | 2/1977 |
| GB | 2353864 | 3/2001 |

* cited by examiner

PRESSURE INDICATOR

The technical field of the invention is that of pressure indicators.

In order to measure the pressure in a fluid, it is known to make said pressurized fluid act against a membrane. The deformation of said membrane is subsequently measured to be processed and displayed to produce a measurement indicative of said pressure. Such a pressure indicator comprises a membrane deformable under the effect of the pressurized fluid. In order to obtain as linear a measurement as possible, the deformable membrane of a pressure indicator always has a high stiffness. This leads, for a given pressure range, for which the pressure indicator is designed, to very small deformations of said membrane. These very small deformations are not directly visible by a human eye and systematically require a gear reduction or amplification device applied to the measurement of the deformation to produce a visible measurement of the pressure. This leads to complex and usually expensive devices.

The invention aims to achieve a simple and inexpensive pressure indicator having small dimensions, so as to be, for example, a single-use device.

The invention relates to a pressure indicator comprising a base, a deformable membrane fixed to the base in a fluid-tight manner according to a closed contour, and a body fixed to the base, delimiting a hollow volume covering the deformable membrane on the side opposite the base, while encompassing at least the closed contour, at least one inlet for a fluid the pressure of which is to be measured in a pressure range, wherein the deformable membrane is such that the expansion thereof for said pressure range is sufficient to be visible to the naked eye and to allow a direct display indicative of the pressure, in that the base is drilled with at least one first hole a first end of which emerges between the deformable membrane and the base in the closed contour, in that the body is drilled with at least one second hole a first end of which emerges into said hollow volume, in that the other end of the first hole is linked to the inlet respectively to the open air, in that the other end of the second hole is linked to the open air, respectively to the inlet, so that a pressure, respectively a pressure reduction, of fluid at the inlet causes an expansion of the deformable membrane in the hollow volume delimited by the body.

In another embodiment, the pressure indicator according to the invention comprises a base, a deformable membrane fixed to the base in a fluid-tight manner according to a closed contour, and a body integral with the base, delimiting a hollow volume covering the deformable membrane on the side opposite the base, while encompassing at least the closed contour, at least one inlet for a fluid the pressure of which is to be measured within a pressure range. The deformable membrane is such that the expansion (E) thereof for said pressure range is sufficient to be visible to the naked eye and enables a direct display indicating the pressure. The base is drilled with at least one first hole, a first end of which emerges between the deformable membrane and the base in the closed contour. The body is drilled with at least one second hole, a first end of which emerges into said hollow volume, and the other end of the first hole is linked to the inlet respectively to the open air, with the other end of the second hole being linked to the open air, respectively to the inlet, so that a pressure, respectively a depression, of fluid at the inlet causes an expansion of the deformable membrane in the hollow volume delimited by the body. The indicator comprises at least two pressure marks, each one facing an expansion position of the deformable membrane, making it possible to determine at least three pressure range values according to said expansion position of the membrane.

Thus, each mark corresponds to a predetermined pressure. The indicator is so configured that, when the expansion of the membrane reaches a mark, the pressure in a chamber positioned on one side of the membrane is equal to the predetermined pressure. Thus, it can be inferred that: when the membrane has not reached the first mark, the pressure to be measured has not reached the first pressure threshold; when the membrane has reached the first mark but has not reached the second mark, the pressure to be measured is between the two pressure thresholds defined by the first and second marks; when the membrane has reached the second mark, the pressure is greater than or equal to the threshold pressure defined by the second mark.

Optionally, the invention may also further have following characteristics:

Preferably, the indicator comprises three or four marks.

Preferably, the body forms a bell. Preferably the bell comprises one or more piece(s). At least one of the parts of the bell is transparent or translucent.

Preferably, the body is fixed to the base.

Preferably, the membrane is elastic.

Preferably, the indicator comprises a single deformable membrane, with the membrane being elastic.

Preferably, the membrane is monolithic. Thus, it is formed of only one layer made of an elastomeric material. It has a homogeneous structure.

Preferably, the pressure indicator is so configured that the membrane, during the expansion thereof, bears against a wall of the body. Preferably, the indicator is so configured that the membrane is gradually spread on the wall as the pressure increases. Preferably, the indicator is so configured that, when the pressure reaches a given pressure, the expansion of the membrane causes a contact of the membrane with the wall, then when the pressure increases, the expansion of the membrane causes the spreading of the membrane on the wall. Preferably, the pressure indicator is so configured that the spreading of the membrane on the wall depends on the pressure to be measured. Optionally, but preferably, the wall extends in a plane substantially parallel to a plane in which the membrane lies when at rest. The membrane takes the pressure difference and may even come into contact with the wall of the bell. The pressure difference is then taken by the bell.

Preferably, the pressure marks each correspond to a spreading of the membrane on the wall. Thus, the user views a gradual spreading of the membrane on the wall. The spreading of the membrane on the wall of the body matches the pressure or depression to be observed. Preferably, the spreading of the membrane on the wall of the body is proportional to the pressure or depression to be observed.

Preferably, the wall is the bottom of a body or a bell forming a volume. It may also be a cover forming the body or partially forming the body.

Optionally and preferably, the wall is flat.

According to an alternative embodiment the wall is domed.

Preferably, the wall is so configured as to prevent a user from viewing the membrane when the membrane is not in contact with the wall and so as to enable a user to view at least a portion of the membrane when the membrane is in contact with the wall. Preferably, the indicator is so configured as to allow viewing of only the portion of the membrane which is in contact with the wall. Preferably, the indicator is so configured as to allow viewing the whole portion of the membrane which is in contact with the wall.

Preferably, the wall is translucent. Preferably, the membrane is opaque.

Preferably, the indicator comprises at least two and preferably at least three marks so arranged as to identify at least three spreading positions of the membrane, and wherein the membrane is spread in the form of a disc on the wall.

Preferably, the marks are so arranged as to view the spreading of the membrane on a single wall.

According to another characteristic of the invention, the expansion of the deformable membrane for the pressure range is at least equal to 1 mm.

According to another characteristic of the invention, the deformable membrane is made of thermoplastic elastomer material of the TPS-SEBS type or SBS type.

The pressure range is between 0-150 cm/H$_2$O and wherein the deformable membrane has a Shore A hardness of 0 and a thickness between 0.3 and 0.8 mm. In a preferred embodiment, the pressure range is 0-120 cm/H$_2$O and wherein the deformable membrane has a Shore A hardness of 0 and a thickness of 0.7 mm. According to another embodiment, the pressure range is 0-100 cm/H$^2$O and the deformable membrane has a Shore A hardness of 0 and a thickness of 0.5 mm.

According to another characteristic of the invention, the deformable membrane comprises, at the closed contour, at least one bead respectively a groove interacting with a groove, respectively a bead, provided in the base.

According to another characteristic of the invention, the deformable membrane comprises, at the closed contour, alternating beads and grooves, cooperating with a respectively corresponding alternating grooves and beads formed in the base.

According to another characteristic of the invention, the material of the deformable membrane comprises a piezochromic compound or a tribochromic compound or a thermochromic compound.

According to another characteristic of the invention, the material of the wall comprises a piezochromic compound or a tribochromic compound or a thermochromic compound.

According to another characteristic of the invention, the bell is at least partially transparent so as to make the expansion of the deformable membrane visible from the outside.

According to another characteristic of the invention, the bell comprises at least one mark facing an expansion position of the deformable membrane, and indicative of the fluid pressure corresponding to said expansion position.

According to another characteristic of the invention, the bell further has at least one distorting lens so as to change the viewing of the expanded deformable membrane.

According to another characteristic of the invention, the distorting lens is arranged with its optical axis perpendicular to the main axis of expansion.

According to another characteristic of the invention, the distorting lens is positioned with the optical axis thereof being parallel to the main axis of expansion.

According to another characteristic of the invention, the bell has a proximal end attached to the base, a distal end and a body extending between the proximal and distal ends. According to one option, the distorting lens is located on the body. Alternately or in combination with this option, the distorting lens is located on the distal end.

According to another characteristic of the invention, the bell presses the deformable membrane against the base at the closed contour.

The invention further relates to the use of such a pressure indicator to monitor pressure in an inflatable pad of a medical device, such as the pad of a laryngeal mask.

The invention also relates to a medical device comprising a pressure indicator according to the invention and an inflatable pad associated with the indicator to monitor the pad pressure.

According to an advantageous embodiment, the device forms a laryngeal mask.

The invention also relates to a medical device for an epidural injection comprising a pressure indicator according to the invention and wherein one of the first and the second hole is in fluid communication with a distal port of a needle for an epidural injection. Advantageously, the medical device includes a needle for an epidural injection.

Other characteristics, details and advantages of the invention will become apparent from the detailed description given below for information in connection with the drawings in which.

Figure 1:
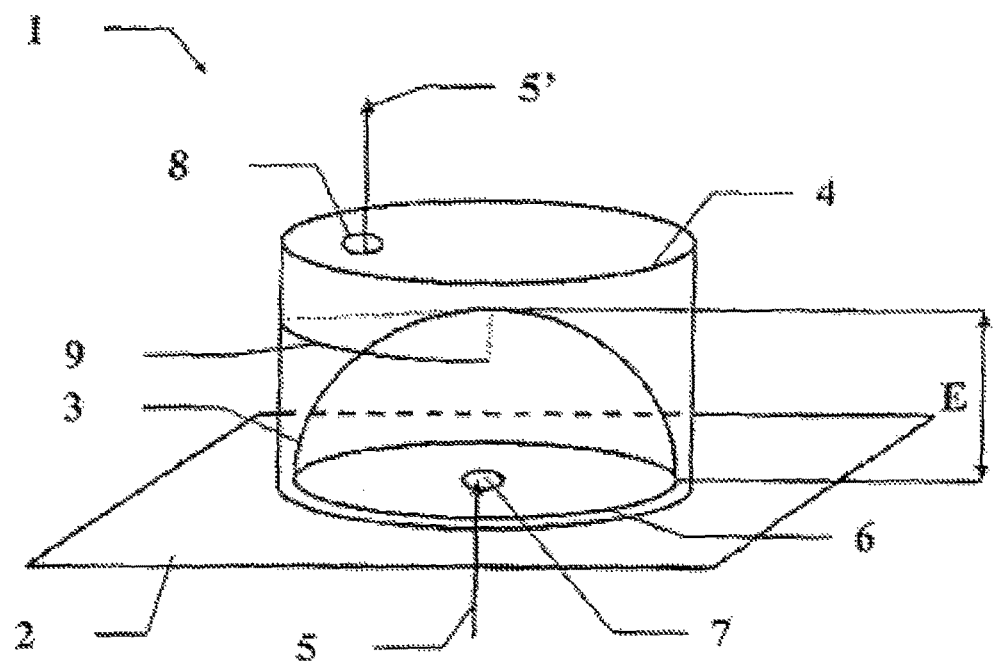
FIG. 1 shows a block diagram of the invention.

FIG. 1 shows a block diagram of the present invention. A pressure indicator 1 essentially comprises a base 2, a deformable membrane 3 and a bell 4 also called a body. The deformable membrane 3 has a surface conformation and is substantially fixed to the base 2 so as to be fluid-tight in a closed outline 6. The surface of the deformable membrane 3 is continuous throughout the interior of said closed contour 6.

The pressure indicator 1 comprises at least an inlet 5, 5'. The inlet 5, 5' allows the fluid connection with a fluid circuit and thus the ingress of a fluid the pressure of which is to be measured. The base 2 comprises at least one first hole 7. One end of said first hole 7 opens between the deformable membrane 3 and the base 2 in the closed outline 6. The bell 4 comprises at least a second hole 8. One end of said second hole 8 opens into said hollow space.

The pressure indicator may have two configurations. In a first configuration, adapted to measure a (positive) pressure, the other end of the first hole 7 is connected to the inlet 5. Thus, the inlet 5 is fluidly connected to the space between the deformable membrane 3 and the base 2 and limited by the closed contour 6, by the first hole 7. Besides, the hollow volume defined by the bell 4 is connected to the open air via the second hole 8. Applying a fluid under a (positive)

pressure to the inlet 5, by pressing the deformable membrane 3, causes the expansion of the deformable membrane 3 in the hollow space of the bell 4.

According to a second configuration adapted to measure a (negative) pressure, the other end of the second hole 8 is connected to the inlet 5'. The inlet 5' is fluidly connected to the hollow space delimited by the bell 4, by the second hole 8. Besides, the space between the deformable membrane 3 and the base 2 and limited by the closed contour 6, is connected to the open air via the first hole 7. Applying a fluid under (negative) depression to the inlet 5' causes an expansion E of the deformable membrane 3 in the hollow volume of the bell 4 by void effect in the hollow space.

The expansion of the deformable membrane 3 always occurs in the same direction, with the deformable membrane 3 filling the hollow volume, under the effect of a positive pressure applied between the base 2 and the deformable membrane 3 or of a negative pressure/depression applied in the hollow volume between the bell 4 and the deformable membrane 3.

A pressure indicator 1 according to the invention may be made according to one of the configurations with an inlet 5 on the base 2 side or an inlet 5' on the bell 4 side. According to an advantageous embodiment, a pressure indicator 1 may be made so as to be compatible with both configurations, including both an inlet 5 on the base 2 side or an inlet 5' on the bell 4 side. The circuit in which it is desired to measure the pressure may then be selectively connected to one or the other of the two inlets 5, 5', depending on the sign of the pressure to be measured, with the other inlet 5, 5', being then left disconnected in the open air.

The base is made of a rigid material. A polycarbonate material is possible.

A pressure indicator 1 is designed for a predetermined pressure range. This pressure range is typically defined between a pressure at rest, corresponding to the ambient pressure (atmospheric pressure) and a maximum positive pressure for the "pressure" configuration or a minimum negative depression for the "depression" configuration.

According to an important characteristic of the invention, the deformable membrane 3 is such that its expansion E for said pressure range is sufficient to be visible to the naked eye. This characteristic advantageously allows direct display, produced by the deformable membrane 3 itself, the expansion E of which is indicative of the pressure reached by the fluid and is directly used as a measurement index. Such a characteristic can be obtained using, for the membrane 3, a material, a shore hardness, a thickness, a shape, making it possible to obtain a high expansion, at least sufficient to be directly visible, when the deformable membrane 3 is exposed to a pressure within the pressure range.

This advantageously allows to avoid gear reduction and/or amplification devices (pantograph, spring, return, electronics, etc.) and display devices (indicator, dial, etc.) otherwise used for pressure gauges. This significantly contributes to simplifying the pressure indicator 1 and thus to reducing the cost thereof.

The pressure indicator 1 also preferably includes one bell 4. Said bell defines a cavity 4. Said bell 4 is attached to the base 2 so as to include the deformable membrane 3 between the base 2 and the bell 4. The deformable membrane 3 is positioned close to the base 2, to which it is attached at least along the closed contour 6, with one of the sides thereof facing said base 2. The other face of the deformable membrane 3, on the side opposite the base 2, faces the hollow volume defined by the bell 4. The bell 4 covers the deformable membrane 3 and includes at least the closed contour 6.

The hollow volume of the bell 4 thus provides a volume for receiving the deformable membrane 3 during the expansion thereof.

To be clearer, an expansion of the deformable membrane 3 may be considered sufficient to be visible to the naked eye when said expansion is at least equal to 1 mm for the pressure range. The pressure range extends from a minimum value of pressure (e.g. the atmospheric pressure) to a maximum absolute pressure. The maximum expansion is typically obtained for the maximum absolute pressure. Such a maximum expansion is preferably at least equal to 1 mm. This relatively low value enables a detection visible by the human eye. This value, however, is significantly higher than the sub-millimeter values of the deformation of rigid membranes of the pressure gauges of the prior art.

This value remains a minimum value. To improve the readability of the pressure indicator, the maximum expansion of the deformable membrane 3 for a pressure range/given maximum pressure is advantageously greater. A maximum expansion value of the order of 10 mm for a pressure range allows easier reading of the pressure indicator 1. A maximum expansion value of about 20 mm is even more comfortable. The higher the absolute maximum expansion value, the easier the reading of the pressure indicator 1. A larger maximum expansion thus increases the number of different marked levels 9 and thus the resolution of the pressure indicator 1. On the contrary, the maximum expansion value determines the overall dimensions in at least one direction of the pressure indicator 1. The admissible overall dimensions thus limits the maximum expansion value.

It should be noted that the very principle of a deformable membrane with a high relative expansion for a given pressure range makes it difficult to obtain a linear expansion E as a function of pressure, mainly because of the used materials having non-linear behaviours in expansion. This more particularly devotes the pressure indicator 1 to uses wherein a comparison/monitoring of a pressure at one or more threshold(s) is desired or to uses requiring only a coarse resolution, rather than uses for a precise measurement proper.

However, the principle of a deformable membrane having a high relative expansion for a given pressure range has a very good repeatability. The repeatability in time ensures the same indication/expansion E for a given applied pressure. The principle of the pressure indicator 1 makes it possible to obtain a measure/indication with a high accuracy/repeatability.

The behaviour of the deformable membrane 3 expanding in response to pressure in a given pressure range mainly depends on the material of the embodiment of the deformable membrane 3, its thickness, and its Shore A hardness and on the surface contained within the closed contour 6, and to a lesser extent on the shape of the closed contour 6 of the possible previous shaping of the working surface 14 of the deformable membrane 3 in said closed contour 6, on the relative thickness distribution. As regards the deformable materials, it is very difficult, or even impossible, to calculate or simulate the expansion. The person skilled in this field uses an empiric approach with successive tests, to determine these parameters. A material, an average thickness, a hardness and a contour 6 surface are thus determined for a pressure range/maximum absolute pressure. Said maximum absolute pressure is applied and produces a maximum expansion which can be compared to the one desired. Depending on the result, the person skilled in the art changes the material, or parameters to obtain said desired maximum expansion.

A candidate material, at least for medium and low pressure for the achievement of the deformable membrane 3 is an elastomer thermoplastic material of the TPS-SEBS type or SBS-type. Such material is available in many shore hardnesses and can be manufactured in various thicknesses to make pressure indicators for a wide pressure range.

According to an illustrative embodiment, corresponding to low pressure, a pressure indicator 1 adapted to a pressure range of 0-100 cm/H$_2$O may advantageously be made with a deformable membrane 3 made of such a material with a Shore A hardness of 0 and a thickness of 0.5 mm. Such an embodiment provides a maximum expansion of 20 mm with a circular closed contour, 15 mm in diameter.

Figure 2:
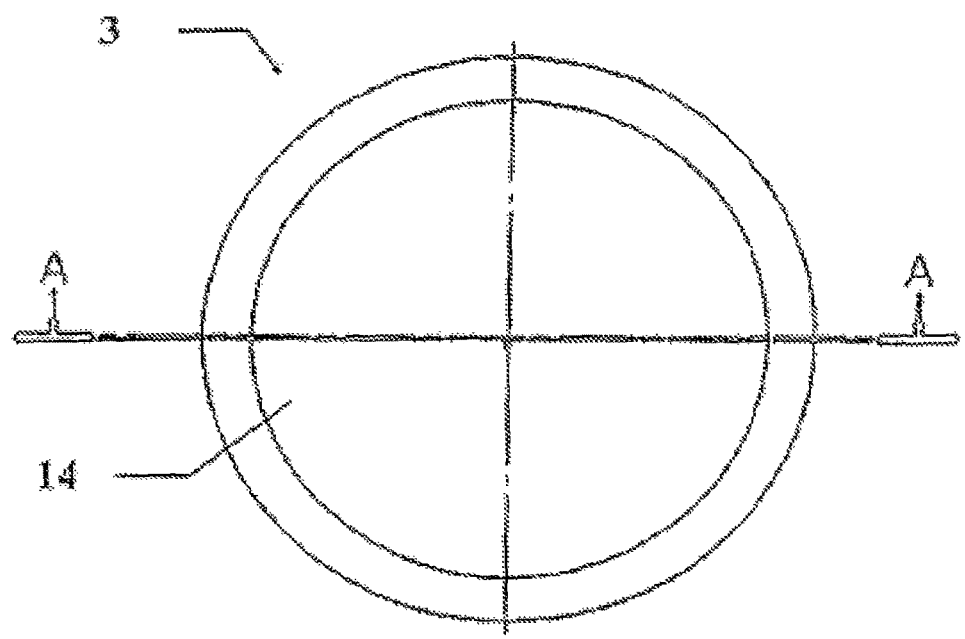
FIG. 2 illustrates a top view of one embodiment of a deformable membrane.
Figure 3:
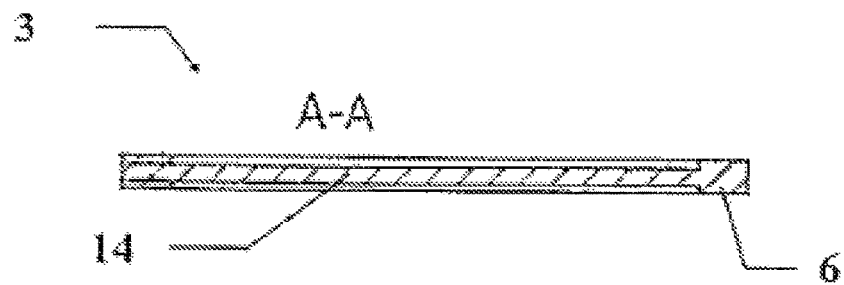
FIG. 3 illustrates a front view of an embodiment of a deformable membrane.

The deformable membrane 3 typically includes a working surface 14 and a closed contour 6. The closed contour 6 may be of any shape. FIGS. 2 and 3 illustrate an embodiment of a deformable membrane 3 with a circular closed contour 6. The shape of the working surface 14, bounded by said closed outline 6 may be obtained by a pre-shaping. A spherical shell pre-shaping may for example be used to facilitate expansion at the beginning thereof. The embodiment shown in FIGS. 2 and 3 shows an initial flat shape.

For the elastomeric materials, the deformable membrane 3 is advantageously made by precision casting, by thermoplastic injection. This provides excellent production reproducibility which advantageously ensures a good reproducibility of pressure measurements from one pressure indicator to another. This allows a mass/large mass-production The deformable membrane 3 is advantageously made in one piece including a useful surface 14 and the closed contour 6, with all possible arrangements.

The deformable membrane 3 must be fixed to the base 2 in fluid-tight manner along the closed contour 6. This attachment can be provided by any means known in the art such as adhesive bonding, welding, clamping, etc.

Figure 4:
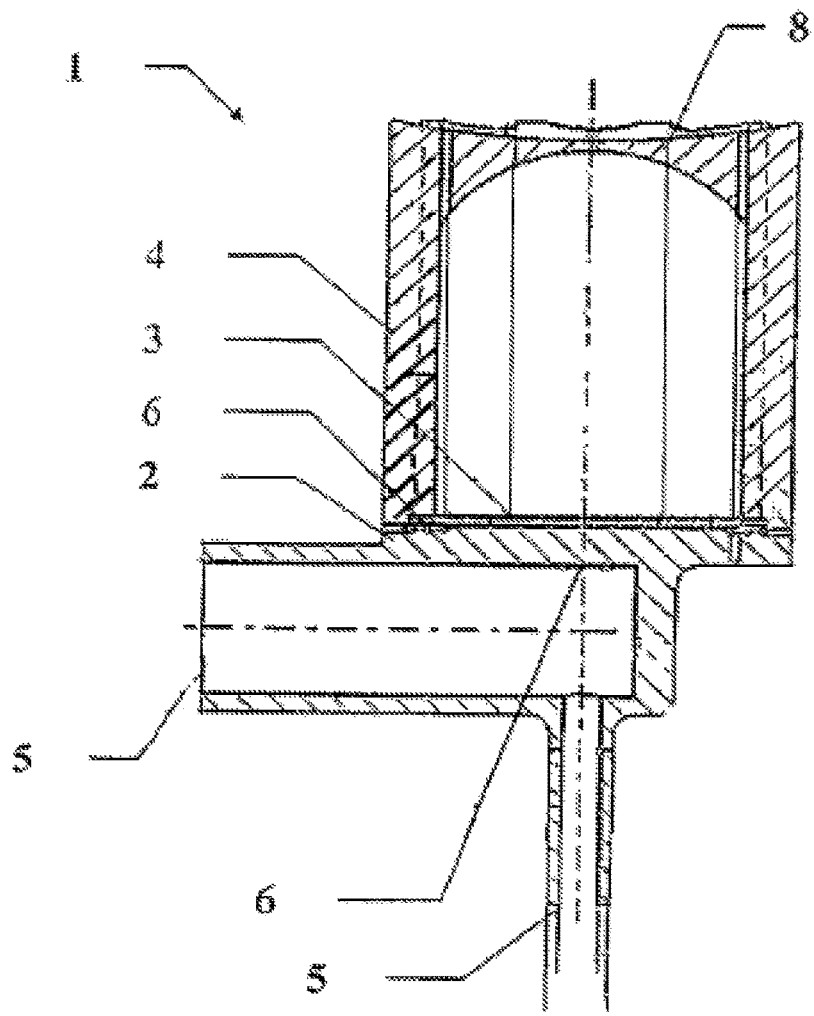
FIG. 4 illustrates a front view of an embodiment of a non-dismountable pressure indicator.

According to an embodiment for example illustrated in FIG. 4, which is particularly advantageous, said attachment is achieved by pressing the closed contour 6, along its entire length, against the base 2. This is preferably facilitated by a path, matching the closed contour 6, provided on a wall of the base 2. In this case the closed outline 6 advantageously has an over-thickness relative to the working surface 14 so that compression is fluid-tight.

According to a preferred embodiment, still shown in FIG. 4, said support is provided by the bell 4. The bell 4 is fixed to the base 2 and is so shaped as to rest on the closed contour 6 against the base 2.

Figure 5:
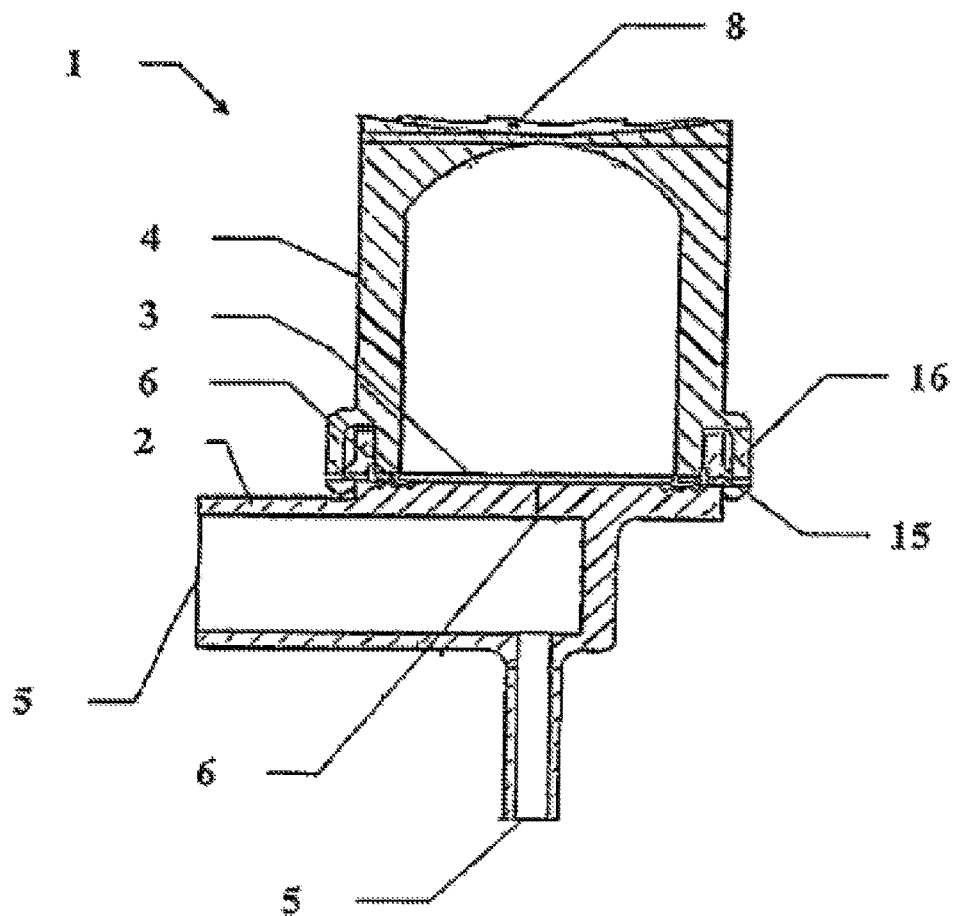
FIG. 5 illustrates a front view of an embodiment of a dismountable pressure indicator.

Fixing the bell 4 on the base 2 can be achieved in different ways. The base 2 and the bell 4 advantageously have matching surfaces to facilitate said assembling. A non-releasable connection as shown in FIG. 4 may be provided. In the example shown the base 2 and the bell 4 include matching opposite bores. The bell 4 is positioned on the base 2. The assembly can then be blocked by any known means: gluing, welding, etc. It is still possible to achieve a dismountable assembly, as shown in FIG. 5. In the example shown, the bell 4 and the base 2 have additional resilient means for an assembly by clipping. The base 2 is provided with a circular pin 15, on which at least one resilient tab 16 of the bell 4 is clipped. The bell 4 can thus be clipped to the base 2. The resilient lugs 16 can be elastically deformed to allow disassembly.

Whatever the assembling mode (gluing, welding, compression/resting, etc.) of the deformable membrane 3 to the base 2, a fluid-tight seal shall be provided between the two parts 2, 3 all along the closed contour 6. This sealing can be provided by the assembling mode itself. This seal can advantageously be enhanced by providing still matching, but not necessarily smooth, opposite surfaces. The deformable membrane 3 thus advantageously comprises, at the closed contour 6, at least a bead interacting with a groove, formed in the base 2. Similarly, the deformable membrane 3 advantageously comprises, at the closed contour 6, at least one groove cooperating with a bead formed in the base 2.

It is still possible to combine several successive bead/groove pairs to further enhance the sealing obtained. Alternating beads and grooves is preferred. And the deformable membrane 3 advantageously comprises, at the closed contour 6, alternating beads and grooves, respectively cooperating with a corresponding alternating grooves and beads formed in the base 2.

Said groove and/or bead are matching and substantially parallel to the closed contour 6. Said groove and/or bead is advantageously made integral with the base 2/the deformable membrane 3, by any means of production: injection, machining, etc.

The bell 4 has several functions. It is possible to distinguish at least one protect function, a mark function, and a saturation/backup function.

A first protect function consists in protecting the volume wherein the deformable membrane 3 expands, so that said expansion does not meet an obstacle. For this purpose, the bell 4 is made of a rigid material that prevents the pressure indicator 1 from being crushed by an element of the environment.

In this function, in this so-called "pressure" configuration, the bell 4, however, should not prevent said expansion of the deformable membrane 3. So as not to produce a counter-pressure which would oppose the expansion, the hollow volume defined by the bell 4 is preferably connected to the open air. This is achieved by said at least one second hole 8 drilled in the thickness of the bell 4 so as to connect the hollow space to the open air. Thus, during the expansion of the deformable membrane 3, the air in the hollow space can escape freely.

Similarly, in the "depression" configuration, the volume between the deformable membrane 3 and the base 2 is advantageously connected to the open air. This is achieved by said at least one first hole 7 drilled in the thickness of the base 2. Thus, during the expansion of the deformable membrane 3, the outside air can freely enter the volume situated between the deformable membrane 3 and the base 2, and thus enable the expansion of the deformable membrane 3.

The first hole(s) 7, respectively second hole(s) 8 jointly have a sufficiently large area to ensure the pressurizing/depressurizing and/or the connection to the open air. However, each first hole 7, respectively second hole 8, individually has a sufficiently small area to prevent the extrusion of the deformable membrane 3 therethrough.

This last characteristic may be provided, including for pressures much lower or much higher than the pressures within the pressure range. The bell 4 then ensures that the deformable membrane 3 can expand neither within nor beyond the hollow space. This advantageously provides protection to the deformable membrane 3, thus preventing the destruction thereof by bursting in case of under pressure or overpressure, including if the sign of the pressure reverses. This provides an advantageous double low and high saturation that performs a pressure indicator 1 backup function.

Another function of the bell, to a lesser extent, is to provide a guiding of the deformable membrane 3 during the expansion thereof. In the absence of a bell 4, the deformable membrane 3 shows spherical expansion. The inner shape of the bell 4, for example cylindrical in FIGS. 4 and 5, forces the deformable membrane 3 to a cylindrical expansion.

Another important function of the bell 4 is to allow referencing of the pressure. For this purpose, the bell 4 is at least partially transparent. The expansion E of the deformable membrane 3 is directly visible from the outside of the indicator 1, and can be observed by a user. The bell 4 is for example made of glass or polycarbonate.

In order to complete this referencing function, the bell 4 advantageously comprises at least one mark 9 facing an expansion position of the deformable membrane 3, indicative of the fluid pressure corresponding to said expansion position. It is thus possible to compare an expansion position E of the deformable membrane 3 with a mark 9 and to get a measure of the relative fluid pressure and this directly against a mark 9 advantageously indicative of a threshold or characteristic pressure level. In reference to FIG. 1, the deformable membrane 3 is in an expansion position corresponding to an expansion E positioning it opposite the mark 9. Since this mark 9 has been previously calibrated, the pressure, respectively the depression, corresponding to this configuration is then determined.

It is thus possible to produce a control, including a mark 9 between two zones or two marks corresponding to two expansion positions and giving an all or nothing indication of the pressure. It is still possible to achieve an indicator 1 comprising n marks 9 and to compare the fluid pressure with the n marks 9. Said n may be any number and is limited only by the longitudinal dimension of the pressure indicator 1 according to the main axis of expansion and the resolution of the user's eye.

Said at least one mark 9 may be provided by any known means. An intaglio or a relief etching, inside or outside the bell 4 is possible. The mark 9 may also be printed or screen-printed. The mark 9 can also be made by colouring/dyeing in the mass or on the surface of the bell 4, or an opaque portion thereof.

Figure 6:
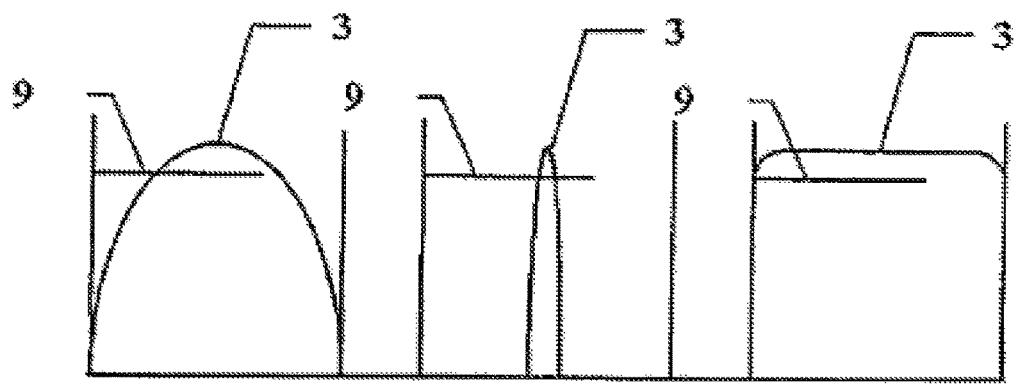
FIG. 6 illustrates different ways of comparing a membrane in expansion with a mark.

Referring to FIG. 6, according to the relative dimensions of the deformable membrane 3 and the bell 4, the distortion of the deformable membrane 3 substantially takes the shape of a spherical dome. The useful part of the deformable membrane 3, which is compared to the marks 9 is domed. This form makes it difficult to compare the position of said dome with the position of a mark 9, as shown in the diagram on the left of FIG. 6.

In order to remedy this drawback, the bell 4 further comprises at least distorting lens 10, 11 so as to change the viewing of the expanded deformable membrane 3. Still referring to FIG. 6, the central diagram illustrates the deformable membrane 3 as viewed through a reducing lens 10, such a cylindrical lens the cylinder axis of which is positioned parallel to the main axis of expansion (vertical in the plane of the figure). Such a reducing lens 10 converts a dome shape of the deformable membrane 3 into a stick shape. The dome is then replaced by the end of said stick, which enables an easier visual comparison with the mark 9.

Figure 7:
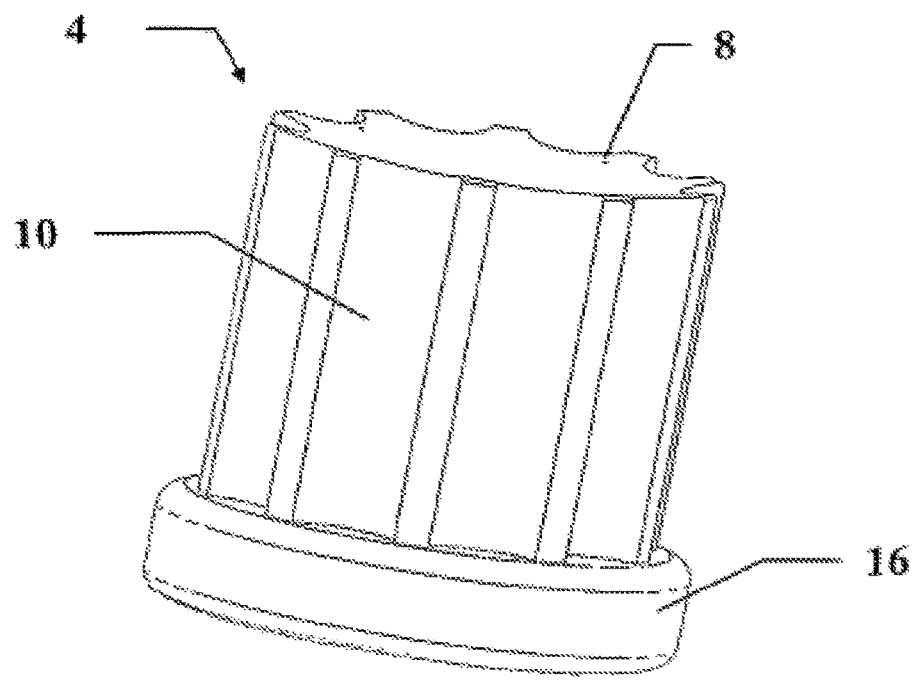
FIG. 7 illustrates an embodiment of a reducing lens

FIG. 7 illustrates, according to one embodiment, a bell 4 including, on the entire periphery thereof, cylindrical reducing lens 10, the cylinder axis of which is positioned parallel to the main axis of expansion.

Still referring to FIG. 6, the diagram on the right shows the deformable membrane 3 as seen through a magnifying lens on 11, such as a cylindrical lens, the cylinder axis of which is positioned perpendicular to the main axis of expansion (in the horizontal plane of the figure). Such a magnifying lens 11 converts a dome shape of the deformable membrane 3 into a plate shape. Said plate enables an easier visual comparison with the mark 9.

Figure 8:
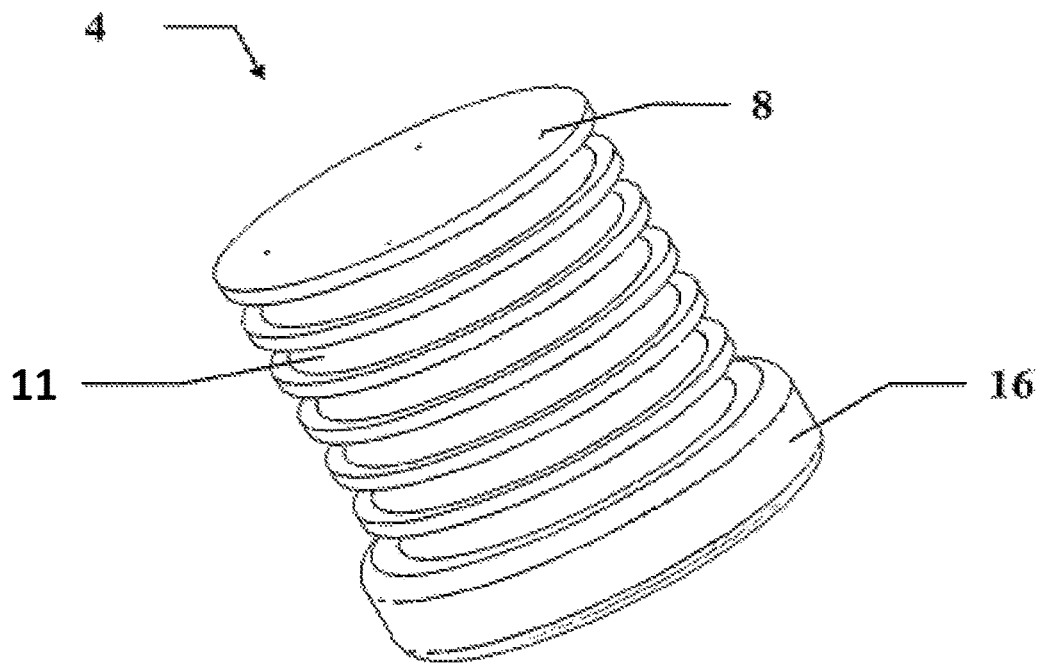
FIG. 8 illustrates an embodiment of a magnifying lens.

FIG. 8 illustrates, according to one embodiment, a bell 4 including, on the whole height thereof, a cylindrical magnifying lens 11 the cylinder axis of which is positioned perpendicular to the main axis of expansion.

In the two previous embodiments, the lenses 10, 11 shall be arranged on the cylindrical wall of the bell 4. They are characterized, in both cases, by a lens optical axis perpendicular to the principal axis of expansion (axis of revolution of the bell 4).

In another embodiment, shown in FIGS. 4, 5, 7 and 8, it is still possible to position a lens the optical axis of which is parallel to the main expansion axis (axis of revolution of the bell 4). This is achieved for example by a concavity at the distal end of the bell 4, visible in the upper part in the plane of the figures. This lens offers a different perspective on the distortion of the deformable membrane 3, which can be very significant in relation to a change in pressure.

To replace, or complete, the indication of pressure obtained by comparing the expansion E of the deformable membrane 3 with at least a level noted with a mark 9, it is possible to add a visible effect to draw even more the user's attention. Such an effect may for example be a colour change effect.

By integrating a piezochromic compound or a tribochromic compound into the material of the deformable membrane 3, during the production thereof, the deformable membrane 3, when subjected to pressure, in addition to the previously described expansion E and creating a spatial effect, will advantageously undergo a change in colour, creating a chromic effect, thus reinforcing the spatial effect and increasing the chances of drawing the user's attention.

According to another alternative or additional embodiment, it is also possible to integrate a thermochromic compound into the material of the deformable membrane 3, during the production thereof. This enables to complete the function of the pressure indicator 1 with a function of indication of temperature of the fluid observed. This can be very advantageous, for example in a medical monitoring application, wherein the same indicator enables a dual monitoring of pressure and temperature.

Advantageously, the indicator is so configured that the membrane, during its deformation, bears against a wall of the body, and then gradually spreads over this wall as the pressure increases. Thus, the user views a gradual spreading of the membrane on the wall. The spreading of the membrane on the wall of the body matches the pressure or depression to be observed. Preferably, the spreading of the membrane on the wall of the body is proportional to the pressure or depression to be observed.

Preferably, the wall is the bottom of a body or a bell forming a hollow volume. It may also be a cover forming the body or partially forming the body. It is integral with the base of the indicator.

Advantageously, the pressure indicator has marks making it possible to visualize the spreading of the membrane on the wall. These marks each correspond to a predetermined pressure which can be shown on the indicator itself or on an associated element. The user can thus read different levels of pressure by observing the mark reached by the membrane portion in contact with the wall. Depending on the disposition and the number of marks, the pressure indicator thus makes it possible to measure pressure.

This embodiment is particularly advantageous since it enables limiting the stress transmitted by the pressurized fluid to the membrane. Indeed this effort, once the membrane is in contact with the wall, is transmitted at least in part to the wall. The membrane deforms less than if there was no contact with the wall. It is thus less prone to fatigue and improves the reproducibility of the measurements even after many uses. This aspect will be explained in greater details below after introducing an embodiment referring to FIGS. 10 to 17.

Advantageously, the pressure indicator is so shaped that the membrane is not visible to the user before making contact with the wall. Thus, the user can see only the portion of the membrane in contact with the wall. The position of the spreading or the evolution of the spreading of the membrane on the surface of the wall can thus be more easily observed.

Figure 10:
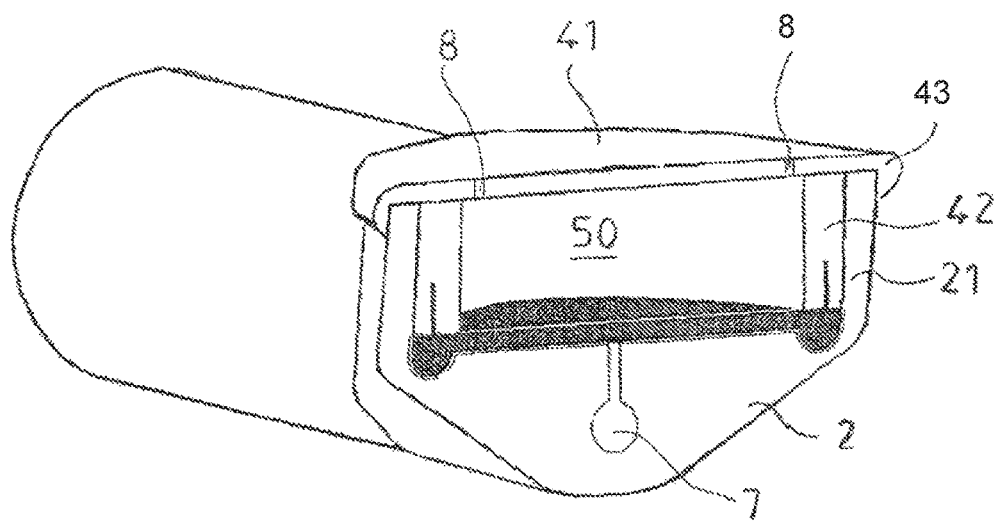
FIGS. 10 to 12 illustrate a cross-sectional view of an embodiment of a pressure indicator according to the invention.
Figure 11:
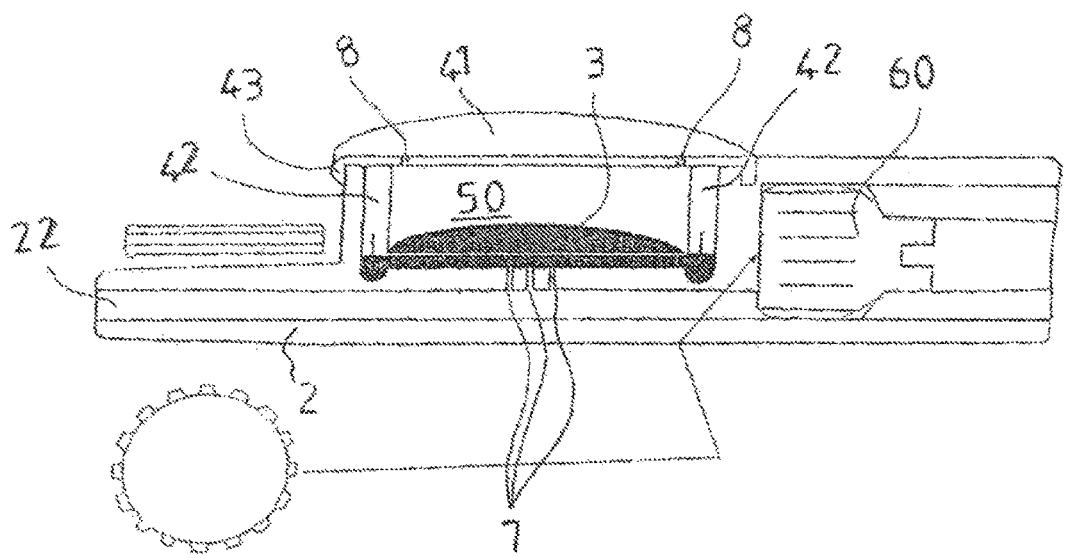
Figure 12:
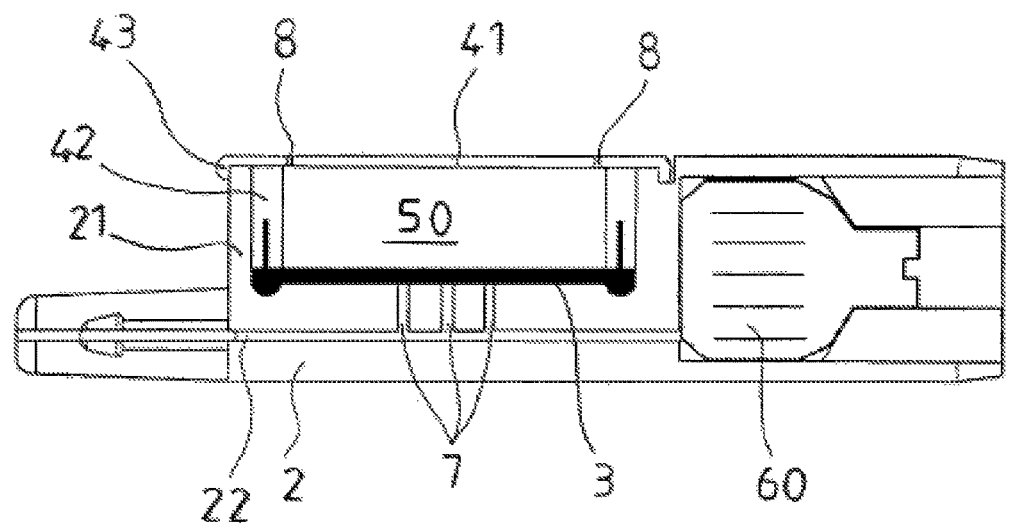

FIGS. 10-12 show a pressure indicator with the characteristics mentioned previously about the other embodiments. In particular, these figures show the membrane 3 inserted between a part 42 of the body and the base 2. In this example, the body includes a part 42, for example having a cylindrical shape and preferably a circular cross-section and a cover 41 blocking and end of the part 42. The upper face of the membrane 3, the part 42 and the cover 41 define a first hollow space 50, also referred to as the first chamber into which the membrane may deform under the effect of pressure. The body comprises at least one hole 8 for a first connection with the hollow space 50 with the ambient air, or with a chamber, the pressure of which is to be measured. In the example shown, the cover 41 has a hole 8 in communication to the open air to hold the first hollow space 50 at the atmospheric pressure. Preferably, the cover 41 includes a plurality of holes 8. The connection between the membrane 3 and the part 42 is tight.

The base 2 has at least one hole 7, preferably several holes, as illustrated in FIG. 11 in fluid communication with a conduit 22, itself in fluid communication with the chamber the pressure of which is to be measured. Advantageously, in rest position, the membrane 3 rests on the base 2. This eliminates or reduces the space between the base 2 and the membrane, thereby reducing the overall dimensions of the pressure indicator. It also makes it possible not to expose the membrane 3 to a permanent load due to its mass.

Advantageously, the duct 22 is a through duct and a valve 60 may be provided to block the conduit 22 downstream of the holes 7.

In the example illustrated, the base 2 has a housing defined by walls 21. The housing is so configured as to accommodate the part 42 of the body. Preferably, the cover 41 is fixed to the housing. Robustness and compactness of the indicator are thus improved. This fixing includes for example a clip, gluing and/or screwing. Edges 43 provided on the cover 41 contribute to this fixing.

Figure 13:
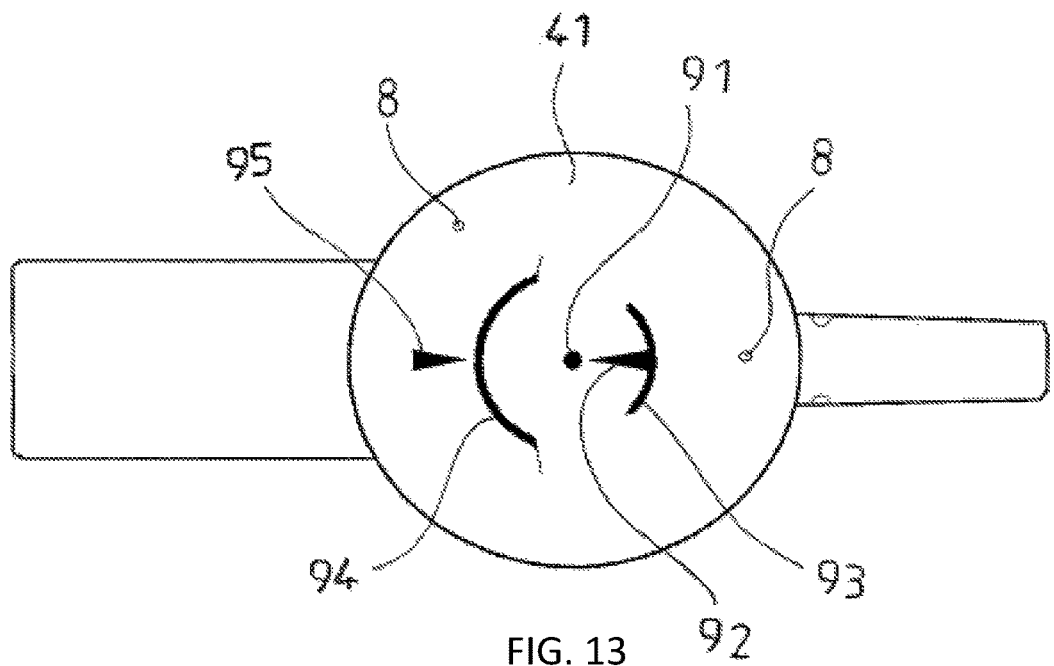
FIG. 13 is a top view of a pressure indicator according to the embodiment illustrated in FIG. 10, FIGS. 14 to 17 are identical to the views of FIG. 13 and show various displays visible by the user when the membrane is subjected to increasing pressure.

As shown in FIGS. 13 to 17, the body bears marks 91, 92, 93, 94, 95 all visible in FIG. 13. As previously stated, such marks are, for example, screen-printed, glued or engraved on the body.

Thus, the pressure indicator according to the invention is based on direct viewing of the deformation of an elastomeric membrane in order to indicate levels of vacuum/pressure in a circuit to a user without having to use a complex mechanism for the amplification of a low amplitude distortion. The pressure indicator according to the invention then requires a significant deformation of the membrane to be perceived by the human eye and consequently a high flexibility of the membrane especially when it comes to measuring low pressures. However, any flexible material of the elastomeric or any other type subjected to constant deformations, successive and continuous stretching/contractions is exposed to more or less fatigue, which results in pressure measurements being relatively uncertain, imprecise and non-recurring in time. To secure the information on the pressure levels transmitted by the pressure indicator according to the invention, i.e. to ensure linearity and recurring indications corresponding to the various levels of pressure values, the invention provides to voluntarily limit the deformation of the flexible membrane, but without increasing the stiffness of the membrane and with no addition of gear reducing and motion amplifying devices like the solutions of the prior art.

To this end, the invention provides an extreme limitation of the extension height of the membrane 3 exposed to pressure. In this embodiment, the maximum deformation of the membrane 3 is controlled and obliged to confine to a range of expansion occurring prior to the starting of fatigue of the flexible material and this, independently and regardless of the value of the pressure applied.

This particular production mode thus ensures an optimal recurrence of the structural shape of the membrane 3 distortion when it is sequentially exposed to various levels of fluid pressure and a clear visual perception to the naked eye, without the addition of gear reducing or amplifying units.

With this structure of the indicator according to the invention, the elastomeric material of the membrane is then capable of supporting a very large, if not almost unlimited number of sequences of inflations and deflations, within any time range, without change over time of the structural shape of its deformation while enabling the user to view a large amplitude of distortion according to the levels of pressure applied, on the bell lid.

This manufacturing method represents a major advance in technology because it solves the problem, unsolved to date, of elastic materials in that they have limited fatigue resistance when subjected to constant stretching/contraction sequences. As a matter of fact, this characteristic of the invention makes the elastomeric membrane almost insensitive to any material fatigue and enables to obtain a constant kinematics of the distortions structural shape whatever the duration and pressure it is exposed to, while allowing a wide viewing of the deformations according to the pressure levels applied.

With this new characteristic, the invention is safer and the pressure indication is more reliable. For this purpose, the elastomer membrane 3 preferably opaque in colour, typically black, is then placed at a short distance from the body cover 41 or more generally from the bell.

Particularly advantageously, the wall against which the membrane expands prevents the viewing of the membrane 3 before this contact is made and enables to view the membrane 3 when the contact is made. Thus, the cover 41 or the ceiling of the bell is made of a rigid and non-transparent material. Preferably, the wall (cover 41 or bell ceiling) against which the membrane is intended to contact and on which it will spread is translucent so as to prevent the user to view the membrane parts that are not in contact therewith. This wall is preferably white in colour for an optimal contrast with the black membrane.

The membrane 3 at rest (not inflated), thus without any contact with the surface of the lid is then almost invisible from the outside of the device to the user's eye because it is hidden by the translucency of the wall 41 material which stands as a screen to the transmission of light toward the interior of the hollow volume 50 and thus hides the membrane 3 which is not exposed to pressure then. the membrane is then moved by the action of the fluid pressure, and comes immediately in contact effortlessly with the internal underside of the translucent wall. Naturally, the first contact between the wall and the membrane is always at the same point, typically at the centre of the lid or the circular ceiling of the bell. When contact is established, the user can see a dark grey or black dot at this point of the translucent wall of the ceiling of the bell.

Then, the more the pressure of the fluid increases, the more the membrane spreads on the internal face of the wall. The indicator is preferably so configured that the whole portion of the membrane in contact with the wall is visible to the user and that the membrane portion which is not in contact with the wall is not visible or is not clearly visible. The membrane spreads for example in a circular manner on the inner wall of the cover then freely increases, for example from a 0 to a 15 mm diameter at pressures of 0 to 120 cm/$H_2O$. In this particular and innovative configuration, the flexible membrane material is not exposed to fatigue because the pressure resultant force is directly transferred to the rigid material of the body wall.

The user then sees the black central initial point extend from the centre of the white translucent outer surface of the cover 41 to the outer edges defined by the circumference of the latter. Under a maximum pressure, the functional surface of the lid becomes totally black.

The surface of the cover may then be provided with graduations for visually transmitting to the user an indication of the actual value of the fluid pressure.

FIGS. 13 to 17 illustrate various pressure levels which can be measured by the indicator according to the invention.

In FIG. 13, the wall 41 shows all the marks 91-95. The membrane is not shown, which means that the pressure to be measured is lower than the pressure corresponding to the mark 91.

Figure 14:
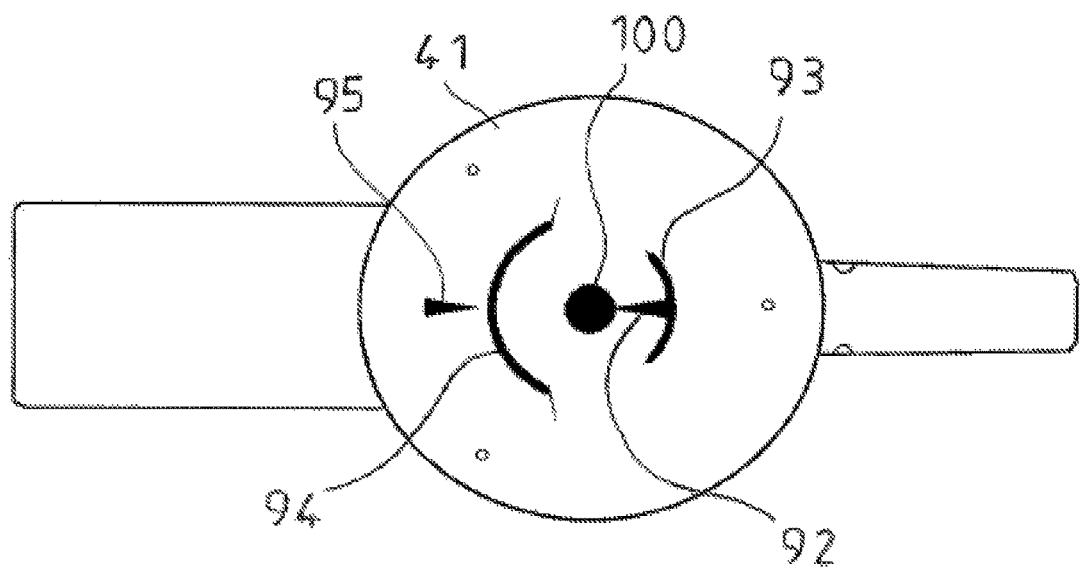

In FIG. 14, a spot 100 is shown. This viewing is enabled by the contact between the membrane 3 and the inner face of the wall 41. The surface of the spot corresponds to the surface of membrane portion 3 which is in contact with the inner face of the wall 41. The mark 92 is flush with the spot 100 and makes it possible to read that the pressure to be measured is equal to the pressure associated with the mark 92.

Figure 15:
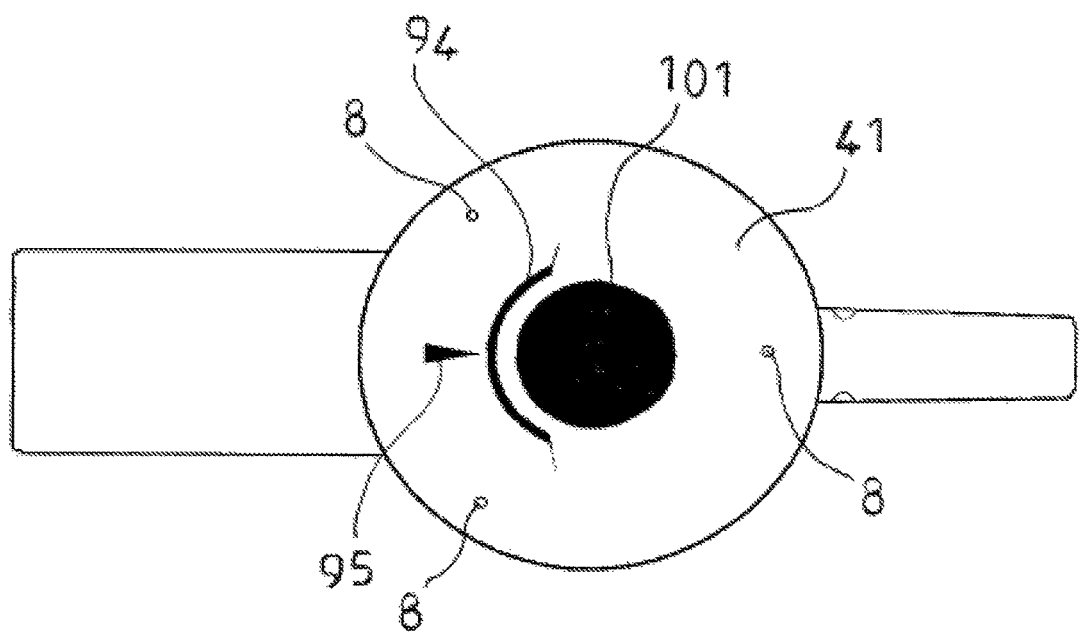
Figure 16:
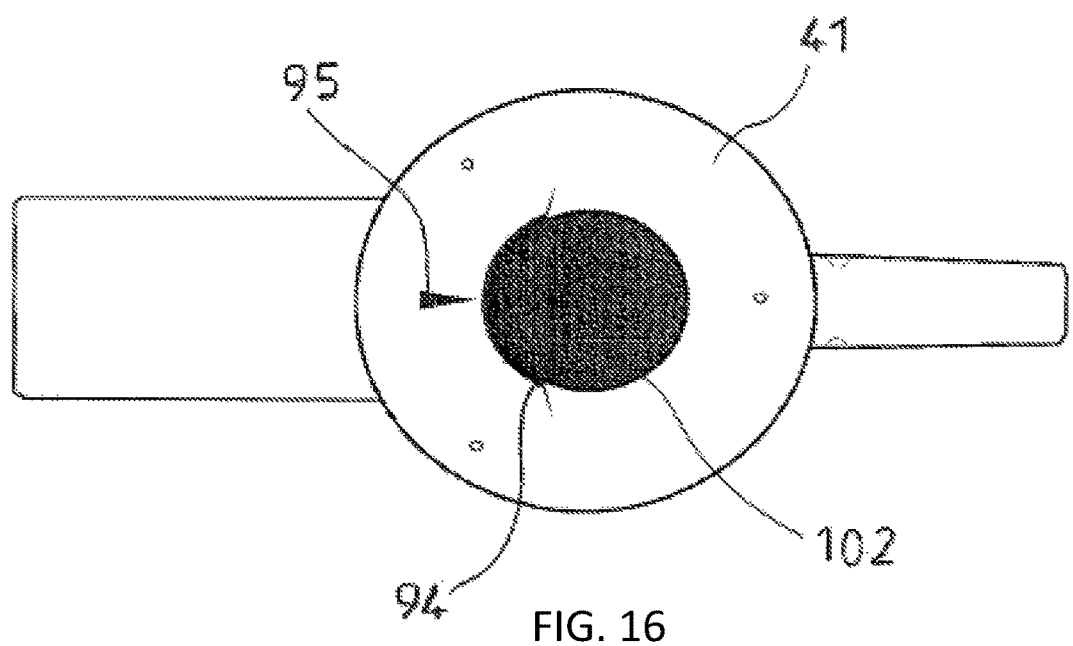

In FIG. 15, the spot 101 has spread and is flush with the mark 93, which means that the pressure in the chamber is equal to the pressure associated with the mark 93. As the pressure to be measured increases, the membrane stretches and spreads on the wall 41. The surface of the spreading increases and reaches the mark 94 as shown in FIG. 16, which means that the pressure to be measured is equal to the pressure associated with the mark 94.

Figure 17:
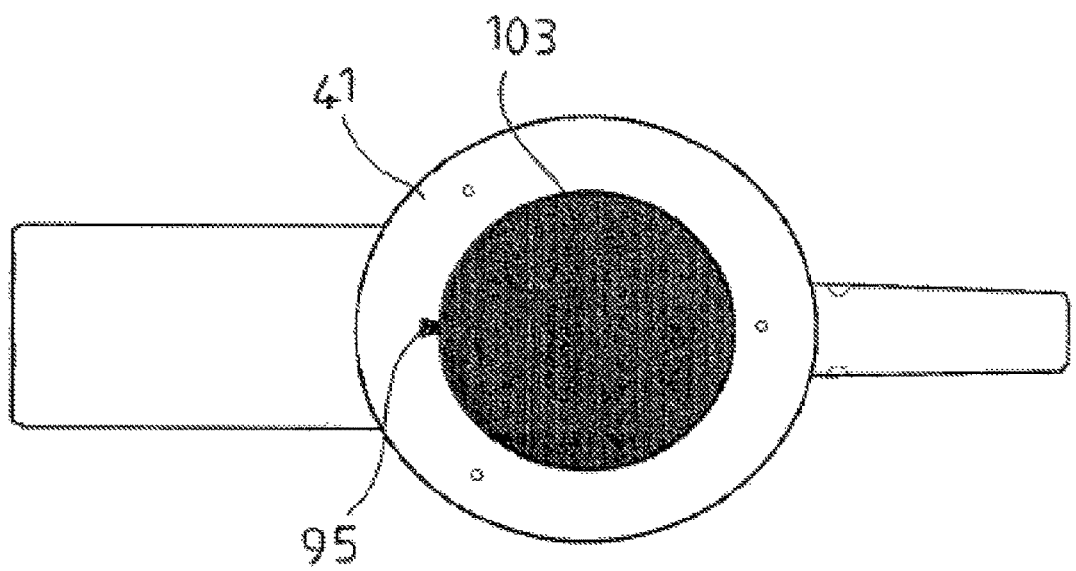

In FIG. 17, the pressure to be measured has reached the pressure associated with the mark 95.

The membrane can thus extend until it reaches all the walls defining the hollow space 50. As such hollow space 50 is bounded by rigid walls, this volume is constant whatever the pressure to be measured. Thus, the invention enables to restrict the expansion of the membrane to a volume equal to that of the chamber 50 whatever the pressure to be measured. Selecting a membrane the plastic distortion limit of which is greater than the volume of the chamber 50 guarantees that the membrane will remain elastic. Thus, even if the pressure to be measured exceeds a recommended operating pressure, the membrane will not be affected and the measures will still be as reliable.

In this embodiment, for example, it may be provided to arrange the membrane at less than 5 mm from the wall to identify pressures ranging from 0 to 120 cm/$H_2O$. Preferably, the deformable membrane has a Shore A hardness of 0 and a thickness of 0.7 mm. The disks visible on the surface of the wall 41 will have a diameter between 0 and 15 millimeters.

All the characteristics mentioned above, especially as regards the materials to form the membrane, also apply to this embodiment.

The invention also extends to non-translucent walls, which enable to mask the membrane in the absence of contact between the latter and the wall and which enable a user to view the membrane when the latter is in contact with the wall. Preferably, the wall enables to display only the membrane portion in contact with the wall.

Thus, in addition to the translucent walls, the invention extends to the walls which prevent viewing the membrane by light reflection, a reflection which is reduced or deleted when the membrane is in contact with a face of the wall.

The invention also extends to indicators wherein the wall coming in contact with the membrane is not a wall substantially parallel to the membrane in the rest position thereof.

The production of such a pressure indicator 1 requires few, typically three parts. These parts can easily be mass-produced and make it possible to obtain a little expensive product. It is thus possible to achieve a single-use pressure indicator 1, which is especially valuable for medical applications.

Moreover, the principle of the invention by expansion of a deformable membrane 3 enables to produce a pressure indicator with very small overall dimensions.

The principle of the invention, wherein the membrane has a very small mass relative to the measured pressure, makes it possible to disregard the effects of gravity. The result is that a pressure indicator 1 according to the invention is advantageously insensitive to orientation and can be used in any position/orientation.

Figure 9:
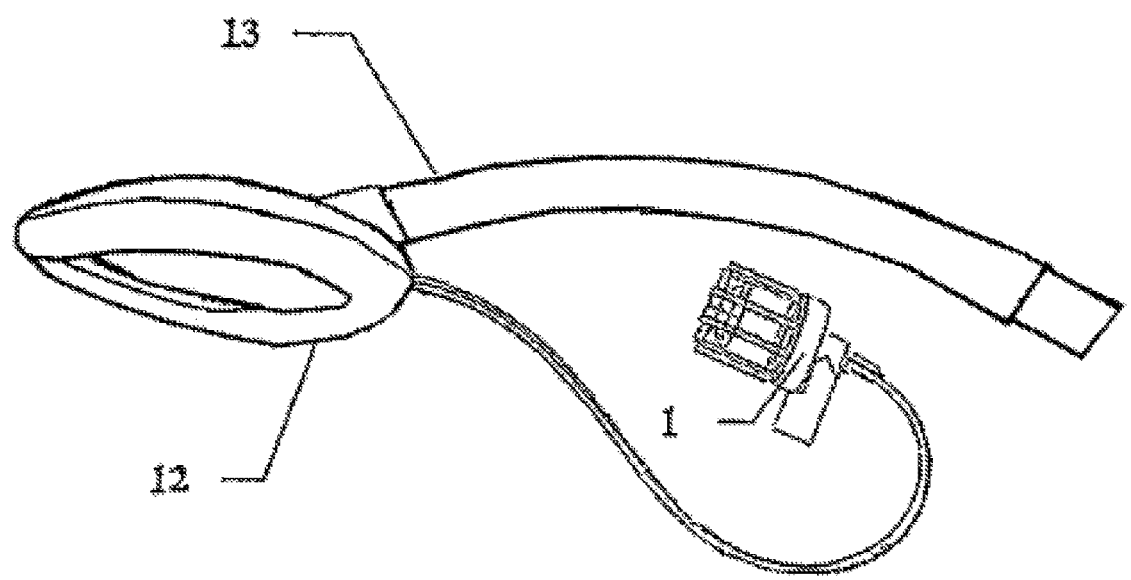
FIG. 9 illustrates one use.

Such a pressure indicator 1 can be used in many applications. A particularly advantageous application in the medical field for any pressure/depression monitoring application in low pressure ranges. It is thus known to use inflatable pads for respiratory intubation devices FIG. 9 shows an example wherein such a device is a laryngeal mask 13 covering the opening of the larynx after positioning into a patient's buccal cavity. An inflatable pad 12 provides the sealing of such a device. The pad 12 must be sufficiently inflated to ensure such sealing. However, the areas of the buccal cavity whereon said pad 12 rests are critical in that they comprise cerebral arteries. Too high pressure on these arteries might cause irreversible brain damage and therefore must imperatively be avoided.

A pressure indicator 1 according to the invention adapted to a pressure range of 0-100 cm/H2O is advantageously tapped onto the pad 12 for monitoring the pressure in the pad 12, and thus the load pressure on the patient's buccal cavity, during the inflation thereof. Such a pressure indicator 1 is advantageously equipped with at least two marks 9. A first mark corresponds to a minimum pressure of inflation of the pad 12 and to a value of 40 cm/H2O. A second mark is a physiological damage threshold pressure not to be exceeded and to a value of 80 cm/H2O. Thus, thanks to the invention, an operator can efficiently check the positioning and the inflating of the pad 12, in complete safety for the patient.

The invention extends to many devices wherein the indicator according to the invention can be integrated. For example, the indicator according to the invention can also be built in a device to perform an epidural injection. The pressure indicator is then used in combination with a needle for an epidural injection. It is more specifically designed to confirm the position of the bevel of the needle in the epidural space. One of the two holes of the indicator is in fluid communication with the distal port of the needle of an epidural injection syringe. The raising of the pressure in the closed system and the deflation of the membrane inform the practitioner that the bevel of the needle has penetrated into a void or that the system is opened for another reason. The practitioner is thus informed that the bevel of the needle has penetrated into the epidural space.

This application for an epidural injection is applicable to all the embodiments described above.

Although a preferred embodiment of the invention has been described in the present, it should be understood that the invention is not restricted to this embodiment, and that modifications may be brought therein within the scope of the following claims.

The invention claimed is:

1. A pressure indicator for use with an inflatable medical device, the pressure indicator comprising:
   a base including a membrane contact surface, a cylindrical wall surrounding the membrane contact surface, a circular groove on the base and adjacent to the cylindrical wall, a duct having an inlet port, and a first hole extending from the membrane contact surface to the duct, the inlet port adapted to be fluidly coupled to the inflatable medical device to produce a pressure at the first hole when the inflatable medical device is inflated;
   a membrane having a circumferential bead and fixed to the base in a fluid-tight manner according to a closed contour and laying on the membrane contact surface when the inflatable medical device is deflated, wherein the membrane is deformable and configured to expand away from the membrane contact surface when the medical device is inflated;
   a body fixed to the base to form a chamber delimiting a hollow volume covering the membrane, the body including a cover overlaying the membrane, a distorting lens positioned with the optical axis thereof being perpendicular to the membrane contact surface, a cylindrical wall extending from the cover toward the membrane, a first pressure mark, and a second pressure mark, the first pressure mark and the second pressure mark defining three pressure ranges, wherein at least one of the membrane and the body comprises at least one of a piezochromic compound, a tribochromic compound, and a thermochromic compound; and
   a second hole fluidly connecting the hollow volume with open air,
   wherein an external surface of the cylindrical wall of the body contacts an internal surface of the cylindrical wall of the base to secure the base to the body and the cylindrical wall of the body presses the circumferential bead of the membrane onto the circular groove on the base to fix the membrane to the base in the fluid-tight manner,
   wherein the membrane is made of thermoplastic elastomer material of the TPS-SEBS type or SBS type,
   wherein the chamber is sized and configured to confine expansion of the membrane to prevent start of fatigue of the membrane,
   wherein the pressure at the first hole causes expansion of the membrane into the hollow volume defining a contact area related to the pressure and discernible by a naked eye of a user, and
   wherein the pressure is in a first pressure range when the contact area does not overlap the first pressure mark, the pressure is in a second pressure range when the contact area is discernible between the first pressure mark and the second pressure mark, and the pressure exceeds the second pressure range when the contact area is discernible beyond the second pressure mark.

2. A pressure indicator according to claim 1, wherein expansion of the membrane for a given pressure range perpendicularly to the membrane contact surface is at least equal to 1 mm and a distance from the membrane to the cover is at most less than 5 mm, and wherein an internal diameter of the cover is at most 15 mm, the distance and the diameter configured to confine the expansion of the membrane.

3. A pressure indicator according to claim 1, the membrane comprising a single membrane, with the single membrane being elastic.

4. A pressure indicator according to claim 1, wherein the membrane is monolithic.

5. A pressure indicator according to claim 1, wherein the base and the body are sized to permit expansion of the membrane up to and including a maximum pressure of 150 cm/H2O, and wherein the membrane has a Shore A hardness of 0 and a thickness between 0.3 and 0.8 mm.

6. A pressure indicator according to claim 1, wherein the base and the body are sized to permit expansion of the membrane up to and including a maximum pressure of 120 cm/H2O and wherein the membrane has a Shore A hardness of 0 and a thickness of 0.7 mm.

7. A pressure indicator according to claim 1, wherein the body further comprises a distorting lens so as to change a view of the contact area, wherein the first pressure mark and the second pressure mark are positioned on the cylindrical wall of the body.

8. A pressure indicator according to claim 1, the duct further comprising an outlet port, the first hole intermediate the inlet port and the outlet port, and the pressure indicator further comprising a valve intermediate the first hole and the outlet port, the valve configured to inflate the inflatable medical device.

9. A pressure indicator according to claim 1, further comprising a cylindrical reducing lens.

10. A pressure indicator according to claim 1, further comprising a cylindrical magnifying lens.

11. A pressure indicator according to claim 1, wherein the body is so configured as to prevent the user from viewing the membrane when the membrane is not in contact with the body and so as to enable the user to view at least a portion of the membrane when the membrane is in contact with the body.

12. A pressure indicator according to claim 11, wherein the body is so configured as to allow viewing of only the portion of the membrane which is in contact with the wall.

13. A pressure indicator according to claim 12, wherein the body is so configured as to allow viewing the whole portion of the membrane which is in contact with the wall.

14. A pressure indicator according to claim 1, wherein the cover extends in a plane substantially parallel to a plane in which the membrane contact surface of the body lies, wherein the first pressure mark and the second pressure mark are positioned on the cover, and wherein the contact area is shaped as a disc on the cover.

15. A pressure indicator according to claim 14, wherein the cover is translucent.

16. A method of monitoring pressure in a medical device, the method comprising:
   observing a pressure indicator fluidly coupled to the medical device, the pressure indicator comprising:
      a base including a membrane contact surface, a cylindrical wall surrounding the membrane contact surface, a circular groove on the base and adjacent to the cylindrical wall, a duct having an inlet port, and a first hole extending from the membrane contact surface to the duct, the inlet port fluidly coupled to the medical device to produce a pressure at the first hole;

a membrane having a circumferential bead and fixed to the base in a fluid-tight manner according to a closed contour and laying on the membrane contact surface when the medical device is deflated, wherein the membrane is deformable and configured to expand away from the membrane contact surface;

a body fixed to the base to form a chamber delimiting a hollow volume covering the membrane, the body including a cover overlaying the membrane, a distorting lens positioned with the optical axis thereof being perpendicular to the membrane contact surface, a cylindrical wall extending from the cover toward the membrane, a first pressure mark, and a second pressure mark, the first pressure mark and the second pressure mark defining three pressure ranges, wherein at least one of the membrane and the body comprises at least one of a piezochromic compound, a tribochromic compound, and a thermochromic compound; and a second hole fluidly connecting the hollow volume with open air, wherein the pressure causes expansion of the membrane into the hollow volume defining a contact area related to the pressure at the first hole and discernible by a naked eye of a user, wherein an external surface of the cylindrical wall of the body contacts an internal surface of the cylindrical wall of the base to secure the base to the body and the cylindrical wall of the body presses the circumferential bead of the membrane onto the circular groove on the base to fix the membrane to the base in the fluid-tight manner, wherein the membrane is made of thermoplastic elastomer material of the TPS-SEBS type or SBS type, and wherein the chamber is sized and configured to confine expansion of the membrane to prevent start of fatigue of the membrane;

determining that the pressure is in a first pressure range when the contact area does not overlap the first pressure mark;

determining that the pressure is in a second pressure range when the contact area is discernible between the first pressure mark and the second pressure mark; and determining that the pressure exceeds the second pressure range when the contact area is discernible beyond the second pressure mark.

17. A medical device comprising:

an indicator comprising an inlet port; and a port fluidly connected with the inlet port of the indicator so as to monitor a pressure in the port, wherein the indicator comprises:

a base including a membrane contact surface, a cylindrical wall surrounding the membrane contact surface, a circular groove on the base and adjacent to the cylindrical wall, a duct having the inlet port, and a first hole extending from the membrane contact surface to the duct;

a membrane having a circumferential bead and fixed to the base in a fluid-tight manner according to a closed contour and laying on the membrane contact surface when the medical device is deflated, wherein the membrane is deformable and configured to expand away from the membrane contact surface;

a body fixed to the base to form a chamber delimiting a hollow volume covering the membrane, the body including a cover overlaying the membrane, a distorting lens positioned with the optical axis thereof being perpendicular to the membrane contact surface, a cylindrical wall extending from the cover toward the membrane, a first pressure mark, and a second pressure mark, the first pressure mark and the second pressure mark defining three pressure ranges, wherein at least one of the membrane and the body comprises at least one of a piezochromic compound, a tribochromic compound, and a thermochromic compound; and a second hole fluidly connecting the hollow volume with open air, wherein an external surface of the cylindrical wall of the body contacts an internal surface of the cylindrical wall of the base to secure the base to the body and the cylindrical wall of the body presses the circumferential bead of the membrane onto the circular groove on the base to fix the membrane to the base in the fluid-tight manner, wherein the membrane is made of thermoplastic elastomer material of the TPS-SEBS type or SBS type, wherein the chamber is sized and configured to confine expansion of the membrane to prevent start of fatigue of the membrane, wherein the pressure at the first hole causes expansion of the membrane into the hollow volume defining a contact area related to the pressure and discernible by a naked eye of a user, and wherein the pressure is in a first pressure range when the contact area does not overlap the first pressure mark, the pressure is in a second pressure range when the contact area is discernible between the first pressure mark and the second pressure mark, and the pressure exceeds the second pressure range when the contact area is discernible beyond the second pressure mark.

18. A medical device according to claim 17, the medical device comprising an intubation device including an inflatable cuff fluidly coupled to the port, and the port configured to inflate the inflatable cuff, wherein the indicator indicates the pressure in the inflatable cuff.

19. A medical device according to claim 17, the medical device configured for epidural anesthesia delivery, wherein the medical device comprises a needle for epidural injection, and the needle is in fluid communication with the port.

20. A medical device according to claim 18, the duct further comprising an outlet port, the first hole intermediate the inlet port and the outlet port, and the pressure indicator further comprising a valve intermediate the first hole and the outlet port, the valve configured to inflate the inflatable cuff.

* * * * *